United States Patent [19]

Petrille

[11] 4,017,548

[45] Apr. 12, 1977

[54] BORONTRIFLUORIDE RECOVERY FROM ALKYL PHENOL MIXTURE

[75] Inventor: Dennis G. Petrille, Batavia, Ill.

[73] Assignee: Standard Oil Company (Indiana), Chicago, Ill.

[22] Filed: Oct. 6, 1975

[21] Appl. No.: 619,789

[52] U.S. Cl. .................. 260/606.5 B; 260/624 C; 423/293

[51] Int. Cl.² .......................................... C07F 5/02

[58] Field of Search ............... 260/624 C, 606.5 B; 423/293

[56] References Cited

UNITED STATES PATENTS

| | | | |
|---|---|---|---|
| 2,378,968 | 6/1945 | Axe | 260/606.5 B |
| 2,739,172 | 3/1956 | Peters | 260/624 C |
| 3,000,964 | 9/1961 | Milligan | 260/624 C |
| 3,360,464 | 12/1967 | Otto | 252/51.5 A |
| 3,692,844 | 9/1972 | Hollis et al. | 260/624 C |
| 3,929,749 | 12/1975 | Cooper et al. | 260/606.5 B X |

OTHER PUBLICATIONS

*Chemical Abstracts*, v. 74, 66318u, (1971).

*Primary Examiner*—Helen M. S. Sneed
*Attorney, Agent, or Firm*—Fred R. Ahlers; Arthur G. Gilkes; William T. McClain

[57] ABSTRACT

A mixture of $BF_3$ gas and vapors of an alkane hydrocarbon having a normal boiling point in the range of about 80° to about 125° C are recovered as exhaust from the partial-condensing zone of a stripping system to which is fed 6–25 weight percent of said alkane as a liquid dissolved in the fluid reaction mixture from $BF_3$-phenolate catalyzed alkylation of phenol with 500–3000 M.W. liquid viscous mono-olefinic polymer of propylene or butylene and $BF_3$-free portion of the fluid reaction mixture is withdrawn as liquid from the partial-reboiling zone of said system. The removal of $BF_3$ by use of such stripping operation is successful without boiling a mixture of said alkane and said alkylation reaction mixture.

7 Claims, No Drawings

BORONTRIFLUORIDE RECOVERY FROM ALKYL PHENOL MIXTURE

BACKGROUND OF THE INVENTION

British Pat. Specification No. 481,909, published in 1938, teaches the para directing effect of $BF_3$-phenolate catalysis on the alkylation of phenols with $C_5$–$C_{12}$ mono-olefinic hydrocarbons and polymers thereof, specifically $C_{12}$–$C_{18}$ mono-olefinic polymers, at reaction temperatures in the range of 0° to 100° C. U.S. Pat. No. 2,655,544, issued Oct. 13, 1953, extends said teaching to the alkylation of phenol with $C_{18}$–$C_{24}$ mono-olefinic hydrocarbons. U.S. Pat. No. 3,360,464, issued Dec. 26, 1969, further extends such $BF_3$-phenolate catalysis teaching to the alkylation of phenol with 500 to 3000 molecular weight (i.e., about $C_{36}$ to about $C_{214}$) mono-olefinic hydrocarbons such as a polymer of ethylene, propylene, butylene, isobutylene, or amylene.

British Pat. Specification No. 1,159,368, published July 23, 1969, confirms that the $BF_3$-phenolate catalysis of the alkylation of phenol with a mono-olefinic polymer of propylene or isobutylene of polymer carbon content from 50 to 20,000 (molecular weight range of about 700 to about 280,000) results in an alkylphenol product whose alkyl-substituent is (by infrared spectrum analysis) more than 95% p-alkyl-substituted.

In the foregoing patents, whenever removal of $BF_3$ portion of the $BF_3$-phenolate catalyst is mentioned, the disclosed removal of $BF_3$ from the alkylation reaction mixture is by water and/or caustic washing or by treatment with ammonia or amine to form a filterable ammonium-$BF_3$ solid complex. British Pat. Sepcification No. 481,909 mentions $BF_3$ recovery and reuse without teaching any specific method therefor.

However U.S. Pat. No. 3,000,964, issued Sept. 19, 1961, teaches $BF_3$ recovery from and recycle to the alkylation of phenol with $C_3$ to $C_{20}$ mono-olefinic hydrocarbons in the presence of $BF_3$-phenolate catalyst through the use of an inert hydrocarbon boiling in the range of 30° to 200° C, preferably a $C_5$ to $C_9$ alkane, which, when added to the alkylation reaction mixture, lowers the boiling point of the resulting mixture so it boils at a temperature within the range of 50° to 175° C, preferably from 100° to 175° C, at atmospheric pressure. Such boiling mixture of hydrocarbon entrainer and alkylation reaction mixture is refluxed under distillation conditions whereby $BF_3$-phenolate dissociates, and $BF_3$ gas is carried by hydrocarbon entrainer vapor to a partial-condenser wherein the hydrocarbon entrainer is condensed but remains as a $BF_3$ gas. The hydrocarbon entrainer condensate is returned to the boiling mixture. The $BF_3$ gas is absorbed in liquid phenol at a temperature of 40°–100° C to reform $BF_3$-phenolate catalyst for recycle to the alkylation reaction. The quantity of the hydrocarbon entrainer used to so remove $BF_3$ amounts to 30 to 200 weight percent of the alkylation reaction mixture.

While the $BF_3$ removal technique of the 1961 Patent was useful for the preparation of $C_3$ to $C_{20}$ (43 to 281 M.W.) alkyl-substituted phenol, it would not be a suitable technique for $BF_3$ removal from the fluid reaction mixture obtained from the alkylation of phenol with a 500–3000 M.W. polymer of propylene or butylene because boiling and refluxing of the mixture of entrainer hydrocarbon and such alkylation reaction mixture would occur at temperatures which would cause substantial molecular weight degration of the desired high molecular weight alkylphenol product by fragmentation of the polymeric alkyl-substituent and attendant alkylation of unreacted phenol with the fragments.

Such fragmentation of the phenol's alkyl-substituent derived from the 500–3000 M.W. propylene or butylene polymer also occurs to the polymeric hydrocarbon alkylating agent during the alkylation reaction, as pointed out in British Pat. specification No. 1,159,368. Said patent indicates that both fragmentations are inherent to acidic catalysis required for the alkylation of phenol but teaches that the fragmentations can be minimized by use of $BF_3$-phenolate as the acidic catalyst in amounts of from 0.1 to 0.5 mole per mole of the polymeric alkylating agent and conducting the alkylation reaction within the temperature range of 0° to 60° C. By the use of such alkylation reaction conditions and by use of 1.0 to 3.0 moles of phenol per mole of the 500–3000 M.W. propylene or butylene polymeric hydrocarbon alkylating agent, the resulting fluid reaction mixture contains about 65–85% of 475–1800 M.W. alkyl-substituted phenol product, 2–12% $C_3$–$C_{12}$ alkylphenol by-product mixture, 3–22% phenol, and 2.5 to 6.0% $BF_3$-phenolate. The difference in molecular weight between the 475–2800 M.W. alkyl-substituent and the 500–3000 M.W. polymeric alkylating agent and the formation of the by-product alkylphenol mixture result from $BF_3$-phenolate fragmentation. The alkane component of the fluid alkylation reaction mixture is a molecular species inherent to the polymeric propylene or butylene as will be later described.

The $C_3$ to $C_{20}$ mono-olefinic hydrocarbon alkylating agents used to prepare alkylphenols according to the 1961 Patent mentioned before and its resulting $C_3$–$C_{20}$ alkyl-substituent do not, as far as the teachings of said patent are concerned, undergo fragmentation in the presence of $BF_3$-phenolate catalyst during either the 40° to 120° C alkylation reaction or the boiling of the mixture comprising the hydrocarbon entrainer and the fluid alkylation reaction mixture at the preferred temperature range of 100°–175° C used to remove $BF_3$ from attendant dissociation of $BF_3$-phenolate catalyst.

However, the fluid alkylation reaction mixture from the phenol alkylation with 500–3000 M.W. propylene or butylene polymer alone or combined with 30 to 200 weight percent of $C_5$ to $C_9$ alkane hydrocarbon when heated above 70° C either during reaction or after the completion thereof is accompanied by rather substantial fragmentation of the polymeric alkylating polymer or the desired 474–2800 alkyl-substituent on the alkylphenol product. For example, heating the alkylation reaction mixture containing an 1823 M.W. alkyl-substituted (substituent from butylene polymer) and to a temperature of 70°–71° C before removing the $BF_3$-phenolate catalyst, causes a 72% decrease in molecular weight of the alkylphenol product.

British Pat. No. 1,159,368 establishes that the use of a SAE 5–40 mineral oil reaction diluent for the alkylation of phenol with the 500–3000 M.W. propylene or butylene polymers will further supress fragmentation of the polymeric alkylating hydrocarbon during the alkylation reaction in the presence of 0.1–0.5 mole of $BF_3$-phenolate catalyst even permitting use of alkylation reaction temperatures in the upper portion of the 0°–60° C reaction temperature range, i.e., 45°–60° C, to produce alkylphenol products of molecular weight equal to or higher than the molecular weight of alkylphenol products produced at reaction temperatures in the range of 20°–25° C. The use of mineral oil reaction diluent and 45°–60° C reaction temperature provides optimum product molecular weight in commercially feasible reaction time. Such use of mineral oil reaction diluent also substantially reduces the viscosity of the resulting alkylation reaction mixture. For example, for alkylphenol products of substantially the same molecular weight the products produced had Universal Saybolt Second (SSU) viscosities at 99° C of 17257, 1943 and 985 SSU when the alkylating butylene polymer reactant weight concentrations were 100%, 68% (32% SAE-5W oil), and 60% (40% SAE-5W oil) respectively. Thus the use of mineral oil diluent provided the two advangages of permitting higher reaction temperatures without contributing greater fragmentation of the polymeric alkylating hydrocarbon thus producing lower molecular weight alkylphenol product and providing a much lower viscosity product.

The use of mineral oil reaction diluent is advantageously employed by combining the mineral oil with the propylene or butylene polymer reactant. Such reactants have SSU viscosities at 38° C in the range of 400 to 788,000. By the use of from 30 to 70 weight percent of the crankcase, e.g. SAE-5W to SAE-40 mineral oils based on the polymer in the present inventive process, the transfer of polymer to the alkylation reaction, conduct of the alkylation reaction, processing of said reaction mixture from $BF_3$ removal through recovery and transfer of the high molecular weight alkylphenol product and further use of such product are not flow limited by high fluid viscosity. The SAE-5W and SAE-10W oils have the respective centistoke viscosities at −18° C of below 860 and below 2600. The SAE-20, 30 and 40 oils have centistoke viscosities at 100° C respectively of between 5 and 10; 10 and 13; and 13 and 17.

British Pat. No. 1,159,368 further discloses that the high molecular weight alkylphenol products from the alkylation of phenol with 500–3000 molecular weight propylene or butylene polymers are useful as intermediates for the preparation of a variety of lubricant oil addition agents which, in general, are produced in the presence of mineral oil as reaction medium. Thus the use of mineral oil to reduce viscosity of the polymeric alkylating hydrocarbon and as alkylation reaction diluent is of further advantage in that such diluent need not be removed from the high molecular weight alkylphenol product before its ultimate use in preparing lubricant oil addition agents.

British Pat. No. 1,159,368 teaches the use of a $C_5$–$C_8$ alkanes as solvent for phenol in the preparation of $BF_3$-phenolate catalyst, for the polymer of propylene or butylene, and as reaction diluent. In the illustrations of such uses of alkane diluent the alkane (n-hexane) retained in the reaction mixture after completing the alkylation reaction amounts to from 25 to 60 weight percent based on the other components of the reaction mixture. However, the alkane was not used in any $BF_3$ removal method. Rather $BF_3$ was removed either by water extraction or by reaction with ammonia to form a filterable solid complex.

The 500–3000 M.W. propylene or butylene poymeric alkylating hydrocarbons used to prepare the 475–2800 M.W. alkyl-substituted phenols are commercially available products obtained from propylene or butylene polymerization in the presence of Friedel-Crafts type catalyst. The commercial polymerizations, in general, use $AlCl_3$ or $BF_3$ as catalyst. Such polymerizations produce a product which contains about 5–15 percent saturated alkane molecules and 95–85 percent substantially mono-unsaturated molecules of the same number average ($\overline{M}_n$) molecular weight. The alkane molecules result from hydrogen redistribution during polymerization and have in their hydrocarbon chains the same units as contained in the saturated portion of the mono-unsaturated molecules. The propylene polymers contain repeating saturated isopropylene units with the unsaturated molecular specifies being terminated by a single isopropenyl unit. The butylene polymers are more complex. While the butylene polymers can be prepared by the polymerization of isobutylene, they are, in general commercially prepared by the copolymerization of refinery butene streams which contain both isobutylene and normal butenes or such refinery streams enriched with isobutylene. The isobutylene polymers contain repeating saturated isobutylene (2,2-dimethyl ethylene) units with the unsaturated polymer molecules terminated by a single unsaturated unit. The copolymers of isobutylene and normal butenes have in their saturated chain or saturated chain portion mainly saturated isobutylene units with some normal butylene units concentrated at one end with the unsaturated molecules of the copolymer terminated at the other end by the single unsaturated unit. In the unsaturated molecular species of both the isobutylene polymers and the copolymers of isobutylene and n-butenes, the terminal unsaturated units are trisubstituted or vinylidene units present as the

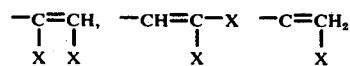

radicals, wherein X is mainly ethyl but also methyl resulting from terminal structure isomerization taking place after the polymerization reaction and before quenching of the catalytic activity.

The alkylation of phenol occurs only by the addition of the foregoing mono-unsaturated molecules to a ring carbon. The addition is mainly (over 95%) to the ring carbon in para position with respect to the ring carbon having the hydroxy-substituent. By such addition to the para-carbon, its hydrogen saturates the single double bond of the foregoing radicals. Thus the product of such addition reaction is an alkylsubstituted phenol, not an alkenylphenol whose substituent retains the double bond.

The foregoing reaction of 1.1–3 moles of phenol catalyzed by 0.1–0.5 mole of $BF_3$-phenolate per mole of 500–3000 $\overline{M}_n$ propylene or butylene polymer diluted with 30 to 70 weight percent of mineral oil produces a viscous fluid alkylation reaction mixture which contains the 475–2800 $\overline{M}_n$ p-alkyl-substituted phenol product, 500–3000 $\overline{M}_n$ alkane, $C_3$–$C_{12}$ alkylsubstituted phenol by-product, unreacted phenol, mineral oil and $BF_3$-phenolate catalyst. Boiling of the mixture of such viscous fluid alkylation reaction mixture and from 30 up to 200 weight percent thereof of an inert $C_5$ to $C_9$ alkane in a distillation column as a means for removing $BF_3$ according to the technique of the 1961 would have no practical value because such boiling, even if possible, would cause drastic molecular weight degradation of the desired 475–2800 $\overline{M}_n$ alkyl-substituted phenol product.

However, it has been discovered that an alkane hydrocarbon having a normal (760 mm Hg) boiling point within the range of 80° to 125° C (hereafter 80°–125° C boiling alkane) can be effectively used to remove BF$_3$ from the viscous fluid alkylation reaction mixture containing the desired 475–2800 $\overline{M}_n$ alkyl-substituted phenol product. Such inventive use of the 80°–125° C boiling alkane does not involve boiling the mixture of such alkane and said viscous liquid alkylation reaction mixture. Rather the inventive use of the 80° 125° C boiling alkane is that of a stripping aid for the removal of dissociated BF$_3$ gas from the viscous fluid alkylation reaction mixture because the relatively high molecular weights of components of the viscous liquid alkylation reaction mixture would not likely boil and reflux at temperatures necessary for dissociation BF$_3$. The present inventive use of the 80°–125° C boiling alkane involves dissolving it in the viscous fluid alkylation reaction mixture and heating incremental portions of the solution to simultaneously dissociate BF$_3$-phenolate and vaporize the dissolved alkane.

Merely adding the alkane to the viscous fluid alkylation reaction mixture will not cause the alkane to become dissolved in a useful short time for continuous operation. Rather such "adding" will, because of the differences in both specific gravities and viscosities, cause the formation of two liquid layers; a top alkane layer and a bottom viscous fluid layer. Vigorous mixing of the liquid alkane and the viscous fluid is required to dissolve the alkane.

Hence, the present inventive BF$_3$ removal is based on an inventive concept differing in kind from the BF$_3$ removal concept of U.S. Pat. No. 3,000,964. Moreover, successful application of the present inventive concept to BF$_3$ removal from the viscous fluid alkylation reaction mixture depends upon technical effects not present in the use of C$_5$–C$_9$ alkanes according to said 1961 Patent.

STATEMENT OF INVENTION

The present inventive concept for the removal of BF$_3$ from the viscous fluid alkylation reaction mixture containing 475–2800 $\overline{M}_n$ alkylsubstituted phenol product and BF$_3$-phenolate catalyst comprises dissolving a 80°–125° C boiling alkane hydrocarbon in such viscous fluid alkylation reaction mixture in an amount of from 6 to 25, preferably 10 to 25, weight percent thereof and heating incremental portions of the resulting solution to a temperature at which BF$_3$-phenolate dissociation and vaporization of said alkane occur. By such operation BF$_3$ gas is stripped from the heated fluid alkylation mixture by vapors of said alkane. The BF$_3$ gas can be converted to BF$_3$-phenolate by adsorbing the BF$_3$ gas in liquid phenol after removing part, 50–95% of the alkane vapor from the BF$_3$-alkane mixture. Since phenol melts at a temperature of 42°–43° C, liquid phenol can, over a temperature range of from 42°–43° C up to 60° C, also rapidly condense and dissolve the 80°–125° C boiling alkane not previously condensed. Such dissolved alkane is inert in the alkylation reaction, is not vaporized at the 45°–60° C alkylation reaction temperature, is thus dissolved in the viscous fluid alkylation reaction mixture at the end of said reaction, and such resulting mixture can with additionally dissolved alkane provide feed for the present inventive BF$_3$ removal process.

Dissociation of BF$_3$-phenolate in the environment of the viscous fluid alkylation reaction mixture apparently does not take place at a precise temperature but rather begins at useful extent at 100° C and proceed more rapidly as temperature is increased. The upper temperature for such dissociation in said environment is not restricted by the rapidity of the dissociation but rather is restricted by the co-stripping of vaporized unreacted phenol by vaporized alkane stripping aid. The stripped phenol vapors also condense as the alkane vapors are condensed. The condensed and/or condensing phenol can react with BF$_3$ and re-form the BF$_3$-phenolate and cause plugging of the condenser and/or its condensate transfer line. Such co-stripping of phenol vapors and be enhanced by the use of an excessive amount of alkane dissolved in viscuous fluid alkylation reaction mixture. By restricting the dissolved alkane to a maximum of 25 weight percent of such viscous fluid and limiting the heating of the incremental portions of such solution of alkane in the viscous liquid to an upper temperature of 130° C the co-stripping of phenol vapors can be minimized to a practical level. The temperature range of from 100° up to 130° C, preferably 120° to 130° C, provided a useful range for heating incremental portions of the stripping feed because it provides a useful BF$_3$-phenolate dissociation and at the same time minimize molecular weight degradation of the desired high molecular weight alkylphenol product.

Because the stripping of BF$_3$ released by dissociation involves mass transfer from the viscous fluid, heating to a temperature of 100° to 130° C of the viscous fluid alkylation reaction mixture containing dissolved alkane must be applied continuously to small incremental portions and not to large portions as in batchwise operation. Batchwise operation would involve heating the viscous fluid containing the alkane from the initial 45°–60° C temperature up to the 100°–130° dissociation temperature which would be too slow to effect rapid dissociation and removal of BF$_3$ from the viscous fluid and would result in drastic molecular weight degradation of the desired high molecular weight alkylphenol product.

Thus heating of the viscous fluid containing dissolved alkane to a temperature in the range of from 100° up to 130° C must be conducted rapidly with incremental portions, i.e., continuously, to effect both rapid dissociation of BF$_3$-phenolate in situ vaporization of the alkane and removal of BF$_3$ gas from the viscous fluid. Suitable means for achieving the rapid heating, vaporizing of alkane in situ and stripping BF$_3$ gas are film flow heating systems which include, for example, flow of the viscous liquid containing dissolve alkane across a heated surface, or over heated trays in a column where the fluid feed is contacted with hot vapors generated by heating the BF$_3$-free portion of the viscous fluid alkylation reaction mixture in the column's reboiler. Such generation of vapors from the BF$_3$-free portion of the fluid alkylation reaction mixture can be accomplished by heating it to a temperature in the range of 150–250°°C at ambient pressure. The BF$_3$-free protion of the fluid alkylation reaction mixture does not boil at such temperatures. Rather, free phenol and other low boiling components of the alkylation reaction mixture are vaporized.

The column can have trays equivalent to 2 to 10 theoretical units for a suitable rapid stripping of BF$_3$-phenolate dissociation and vaporization of the 80–125° C boiling alkane occurs at the feed entry to such column. In such multi-tray efficiency columns, the feed entry can be either at the top unit or a lower unit. Where the feed enters at a unit below the top unit, the upper units can function as a rectification zone for enrichment of BF$_3$-alkane vapors and depletion of phenol and such other low boiling components of the alkane and BF$_3$-free portion of the feed. In such combination of rectification and stripping zones in said columns, it is advantageous to have about one-half of the 80°–125° C boiling alkane stripping aid dissolved in the viscous fluid alkylation reaction mixture and the second half of said alkane stripping aid added as liquid reflux to the rectification zone to further minimize phenol co-stripping.

However, the advantage of the present invention cannot be obtained by "adding" (i.e., any operation not causing dissolving) all of the alkane stripping aid as liquid reflux to the rectification zone or to the stripping zone. Such "adding" of the alkane stripping aid as liquid reflux to the stripping zone or its feed causes the alkane to vaporize without dissolving in the viscous fluid alkylation reaction mixture and thus there is no in situ vaporization of the alkane necessary for rapid stripping dissocaited BF$_3$ gas from the viscous fluid. Such in situ vaporization of the dissolved alkane stripping aid to rapidly remove dissociated BF$_3$ gas from the viscous fluid is a technical effect essential for the successful operation of the present invention.

An additional technical effect in the present inventive BF$_3$ removal process comes from the use of the small amount, 6–25 weight percent, of 80°–125° C boiling alkane. It would not be appreciated from the 1961 Patent that such smaller amount of vapors of such alkane would be sufficient to strip and sweep dissociated BF$_3$ gas from the remainder of the fluid alkylation reaction mixture. The use of such small amount of alkane stripping aid also provides the technical advantage of transferring and processing smaller volumes of gas-vapor mixture.

A still further technical effect in the present inventive process comes from the use of the alkane stripping aid used as reflux liquid to the rectification zone. This technical effect is associated with the nature of commercially available phenol and polymers or propylene or butylene reactants. Such reactants are not commercially available as anhydrous products and it is not commercially feasible to remove all the water from said commercially available reactants. But it is commercially feasible to dry phenol to a water content of 0.05 weight percent and the polymer to a water content of 0.01 weight percent. But such low concentrations of water do present a processing problem in the removal and recovery of BF$_3$ from the viscous fluid reaction mixture.

It is known that BF$_3$ reacts with water to produce HF and boric acid and the HF reacts rapidly with BF3 to produce HBF$_4$. The second reaction is known to be more rapid than the first so that the two reaction steps are generally illustrated by the single equation:

$$4BF_3 + 3H_2O \rightarrow B(OH)_3 + 3HBF_4$$

Since the second reaction does not go to completion, there is also a small amount of HF in the viscous fluid alkylation product.

Thus, when the total water introduced into the BF$_3$-phenolate catalyzed reaction comes from 0.05 weight percent in the phenol and 0.01 weight percent in the propene or butylene polymer, the reaction of water with dissociated BF$_3$ produces HBF$_4$ as a major component of a "red oil complex" which must be removed. Accumulation of said red oil complex results in its downward flow with the BF$_3$-free portion of the viscous fluid to a hotter zone of the stripping zone or to its reboiling zone. The HBF4 in the red oil has been found to decompose at a temperature of 137–138° liberate C and liberte BF$_3$ which causes molecular weight degradation of the desired alkylphenol product and foaming in the stripping zone.

Removal of the red oil complex and minimizing the problems it can cause can be effected by the use of a rectification zone above the stripping zone and by recycling about one-half of the 80°–125° C boiling alkane (5 to 12.5 weight percent based on the viscous fluid alkylation reaction mixture) as reflux to the rectification zone. Such use of the alkane reflux minimizes phenol co-stripping and also concentrates the red oil in the rectification zone for removal therefrom with the BF$_3$ gas-alkane vapor mixture thus assuring that red oil does not flow down below entry of the feed and enhance molecular weight degradation of the desired product. Upon cooling the resulting mixture to condense the alkane vapors, the red oil complex condenses and, being heavier than the alkane condensate, rapidly settles out as a bottom liquid phase. The upper alkane condensate layer can be readily returned to the BF$_3$ gas removal system and the layer of red oil complex can be withdrawn for discard.

From the foregoing it is apparent that, in the conduct of the process of this invention with the commercially dried reactants, one-half of the alkane condensate is recycled to be dissolved in the fluid alkylation reaction mixture and the second half of the condensate is used as liquid reflux to the rectification to concentrate therein the red oil. Thus the total alkane used according to the preferred conduct of the present inventive BF$_3$ removal process is within the preferred range of 10 to 25 weight percent of the viscous fluid alkylation reaction mixture.

The amount of 80°–125° C boiling alkane condensed in the partial-condensation zone can be in the range of 50 to 98 weight percent of that in the BF$_3$ gas-alkane gas mixture.

The advantages of the present inventive concept can be achieved by the use of simple unit operations which comprise, for example, when the alkylation reactants are anhydrous, the combination of a zone for mixing the alkane and viscous fluid reaction mixture to dissolve the alkane therein, a partial-reboiling zone, a stripping zone of efficiency equivalent to five to ten theoretical plates to receive vapors from the partial-reboiling zone to supply heat to dissociate BF$_3$-phenolate catalyst and vaporize the 80°–125° C boiling alkane to aid in stripping BF$_3$ gas, a partial-conensing zone to condense 50–98 percent of said alkane vapors and provide alkane condensate for re-use, and means for transferring the mixture of BF$_3$ gas and uncondensed alkane vapor to fresh molten phenol feed for the alkylation reaction to form in situ, with makeup BF$_3$ gas, the BF$_3$-phenolate catalyst.

When the aforementioned amounts of water are introduced by the reactants into the alkylation reaction, the unit operations include a rectifying zone of efficiency equivalent to three theoretical plates between the stripping zone and the partial-condensing zone. Also the condensate receiving means should have provisions for drawing alkane condensate from a point above the bottom of such receiver and means at the bottom for draining the settled red oil complex.

The selection of alkane hydrocarbon normally boiling in the range of 80°–125° C for use in the present BF$_3$ removal process is made on the basis of technical effects associated with said alkane hydrocarbon. One technical effect is that said alkane hydrocarbon vaporizes at a temperature below molecular weight degradation of the desired alkylphenol product. A second technical effect from use of said alkane is that the $BF_3$-phenolate catalyst dissociates rapidly at a temperature in the range of 100°–130° C, promoting rapid vaporization of the selected alkane.

A third technical effect is related to $BF_3$ recovery for re-use. This can be illustrated on the basis of $BF_3$ recovery factors wherein the $BF_3$ recovery from the use of n-heptane is expressed as 1.0 and based thereon the factor for n-hexane, n-octane or n-nonane is expressed as the proportion of 1.0 represented by the ratio of $BF_3$ recovery from the use of the other n-alkane to $BF_3$ recovery from the use of n-heptane. The $BF_3$ recovery factors determined in association with discovery of the present inventive $BF_3$ removal and recovery method are shown in TABLE I.

TABLE I

| Alkane Hydrocarbon | $BF_3$ Recovery Factor |
| --- | --- |
| n - Heptane (b.p. 98.4° C) | 1.0 |
| n - Hexane (b.p. 68.7° C) | 1.0 |
| n - Octane (b.p. 123.8° C) | 0.62 |
| n - Nonane (b.p. 150° C) | 0.36 |

Alkanes boiling above 125° C, e.g., n-nonane, have low $BF_3$ recovery factors but more important their higher boiling point for vaporization needed for $BF_3$ stripping can contribute to molecular weight degradation of the desired alkylphenol product and excessive phenol stripping. Hence, such higher boiling alkanes have no practical use in the present invention.

The factor for n-pentane was not determined because its boiling point (36.15° C) made its use not feasible for $BF_3$ removal since dissolved n-pentane would not remain a liquid in sufficient concentrations in the viscous fluid alkylation reaction mixture at a temperature in the range of 45°–60° C.

The split of the condensate of the 80°–125° C boiling alkane between reflux to the rectification zone and recycle to the dissolving of the alkane in the viscous fluid alkylation reaction mixture overcomes more than the problems associated with the red oil complex. Providing a portion of the alkane condensate as reflux to the rectification zone also been found to reduce formation of the red oil complex by an amount of about 35 percent by minimizing stripping of free phenol.

By reducing the stripping of phenol and formation of red oil complex and providing its removal from the $BF_3$ recovery system, the present inventive process can achieve higher $BF_3$ recovery than merely increasing the amount of the alkane dissovled in the viscous fluid alkylation reaction mixture.

Typical specific alkane hyrocarbons of normal (760 mm Hg) boiling point in the range of 80°–125° C, include n-heptane; n-octane; 2-methylhexane; 3-methylhexane; 2,4-dimethylhexane; 2,5-dimethylhexane; 2,2-dimethylpentane; 2,4-dimethylpentane; 3,3-dimethylpentane; 3-ethylpentane; 2,2,3-trimethylbutane 2,2,4-trimethylpentane; 2,2,3-trimethylbutane; and 2,3,3,3-tetramethylbutane. The commercial grade and technical grade of n-heptane having the respective 100% distillation ranges of 93°–98.5° C and 97.5°–99.5° C are suitable sources of n-heptane for the $BF_3$ removal process of this invention. Commercial and technical grades of n-octane are also useful sources thereof. Such alkanes have a viscosity and specific gravity much lower than the viscous liquid alkylation reaction mixture. Merely adding the alkane to the viscous liquid alkylation reaction mixture would results in a two liquid phase system. Vigorous mixing of the viscous liquid alkylation reaction mixture and such alkane is required to dissolve the alkane in said viscous liquid.

SPECIFIC EMBODIMENTS

The practice of the present inventive concept to take advantage of all the aforementioned technical effects and advantages can utilize the two systems described before for use when the reactants for the alkylation reaction are anhydrous and when the reactants are dried to water contents which are currently commercially feasible level.

It is preferred to have a two zone column divided into a lower stripping zone of the five theoretical plate efficiency and an upper rectifying zone of the three theoretical plate efficiency. The column and its condenser should be fabricated from metals which can resist the corrosion of $BF_3$ vapor and the red oil complex.

A convenient method for disposing of any HF liberated by or from the red oil complex is to pass the mixture of $BF_3$ gas, alkane vapor and HF over soft glass. The silicon tetrafuoride produced can be absorbed in cold water and the solution discarded.

The present inventive removal of $BF_3$ can be applied to alkylation reaction mixtures produced at temperatures of 45°–60° C by the reaction of the 500-3000 $\overline{M}_n$ viscous liquid polymer of propylene or butylene and phenol used in the proportions of 1–6 moles, preferably 1–4 moles, of phenol per mole of said polymer, in the presence of 0.05 to 0.5 mole of $BF_3$-phenolate catalyst per mole of said polymer and in the presence of 30-70 weight prcent of mineral oil based on said polymer.

The practice of the present inventive process for $BF_3$ removal and recovery is illustrated by the example to follow in which both the alkylation of phenol and the removal and recycle of $BF_3$ are conducted by continuous operations.

EXAMPLE I

For this example the weight of individual process streams are on an hourly basis.

For the alkylation of phenol with a 2000 $\overline{M}_n$ copolymer of mainly isobutylene and some n-butylenes, two feed fluids are prepared. The copolymer feed is prepared as a solution of the copolymer containing 32 weight percent SAE-5W oil (an oil which is free of aromatic hydrocarbons) at a temperature of 52° C. The phenol containing feed is prepared by adding make up $BF_3$ to recovered $BF_3$-heptane mixture to phenol (0.05 wt.% water) at 55° C. to provide 6.43% $BF_3$ and 4.24% heptane content by weight and cooled to 52° C. To a closed, alkylation reaction vessel equipped with an agitator and a cooling jacket there are charge 1250 pounds of the diluted copolymer (3190 cps viscosity at 52° C) and 134.4 pounds of said phenol feed (8.5 cps viscosity at 52° C). The alkylation reaction vessel is operated at ambient pressure and at a temperature of 52° C by supply of coolant liquid to the jacket to remove heat of reaction. Reactant residence time in said reaction vessel is 160 minutes. In such reaction, there are provided 3.0 moles of phenol and 0.3 mole of $BF_3$ per mole of copolymer.

The fluid reaction mixture withdrawn, 1384.4 pounds, contains 0.6% $BF_3$, 5.3% phenol, 41.7% p-alkylphenol product of 1800 $\overline{M}_n$, 1.0% t.amylphenol, 0.6% t.butylphenol as by-products, 50.3% alkane hydrocarbon from the 5W oil and unreacted copolymer, 0.4% heptane an 87 ppm water on a weight basis and has a viscosity of 3100 cps at 52° C.

The fluid alkylation reaction mixture, 1384.2 pounds, at a temperature of 52° C and 102 pounds of recycle heptane containing 1.0 wt.% phenol at 82° C are mixed (viscosity of 1000 cps at 55° C) to dissolve the heptane and provide feed (7.8 wt.% heptane) at 55° C to a column having a partial-reboiling zone, a stripping zone of five theoretical plate efficiency and a rectifying zone of three theoritical plate efficiency. Said 55° C feed enters said column at the top of the stripping zone. The partial-reboiling zone is operated at a temperature of 250° C. Heptane reflux, 102 pounds with 1.0 wt.% phenol content, at a temperature of 82° C is fed (7.4 wt.% on alkylation reaction mixture) to the top of the rectification zone. Vapors (e.g. vapors of phenol, t.amyl- and t.butyl-phenols and low boiling components of 5W oil and polymer alkane) from the partialreboiling zone provide the heat for vaporizing heptane and dissociation of $BF_3$-phenolate in the stripping zone.

The gaseous mixture (vapors of heptane, phenol and red oil complex, and $BF_3$ gas) leaves the top of the column at 101.5° C is air cooled in a partial-condensing zone; the condensate is collected in a condensate receiver to which is added 2.0 pounds fresh heptane at a temperature of 15° C to provide 206 pounds of heptane condensate (1.0% phenol content) for 50:50 split between recycle heptane to be dissolved in fluid alkylation reaction mixture and reflux to the rectification zone. The red oil complex is withdrawn from the bottom of the condensate receiver and is discarded.

The uncondensed gaseous mixture, 12.8 pounds, at a temperature of 65° C (1.07 cubic feet per minute at 65° C) containing 0.49% HF, 54.9% $BF_3$ and 4.6% heptane by weight is contacted with soft glass beads to remove HF in a closed absorber operated at ambient pressure. The glassHF reaction product is withdrawn periodically, dissolved in warm water and the aqueous solution discarded. The mixture of $BF_3$ gas and heptane vapor and make up fresh $BF_3$ (1.7 pounds) are introduced into liquid phenol to provide the fluid phenol feed to the alkylation reaction.

The 1371.6 pounds of fluid withdrawn from the partial reboiling zone is $BF_3$-free, is at a temperature of 250° C and has a viscosity of 530 cps at said temperature. The withdrawn 250° C fluid contains 5.3% phenol, 39.8% p-alkylphenol product of 1700 $\overline{M}_n$, 0.6% t.amyl- and 1.0% t.butyl- phenols, 24.0% polymer alkane 29.2% oil, and 0.1% heptane on a weight basis. Said 250° C fluid is distilled to remove heptane, phenol for recycle to the alkylation reaction and the t.amyl- and t.butyl- phenols for their value as reactants. For example, t.butylphenol and t.amylphenol can be reacted with isobutylene to obtain the hindered phenol anti-oxidants tri(t.butyl) phenol and t.amyl-di(t.butyl)-phenol. The residual liquid from such distillations is a solution containing about 45 wt.% of the p-alkylphenol product of 1700 $\overline{M}_n$.

EXAMPLE II

In this example, phenol in continuously alkylated with a propene polymer of 900 $\overline{M}_n$ in the presence of $BF_3$-phenolates catalyst at a temperature of 96.5° C. The propene polymer undergoes little, about 6%, molecular weight degradation at said temperature. The alkylation reaction is conducted in the same reaction vessel described in Example I to which is fed on an hourly basis 1211.5 pounds of solution of the polymer in SAE-5W oil (68 wt.% copolymer and 32 wt.% SAE-5W oil) at a temperature of 96.5° C and 215.55 pounds of phenol feed (6.8% $BF_3$, 2.5% heptane and 90.7% phenol by weight containing 50 ppm water) at a temperature of 51.5° C. This provides about 1.0 mole of total phenol containing 0.23 mole of $BF_3$-phenolate per mole or propene polymer. The reaction residence time is 160 minutes. The fluid alkylation reaction mixture is produced at 1427.8 pounds per hour and at its temperature of 96.5° C has a viscosity of 224 cps.

The 1427.8 pounds of fluid alkylation reaction mixture with a $BF_3$ content of about 1.0 percent, about 42.3% p-alkylphenol product, and about 1.0% p-alkyl $(C_6)$-substituted phenol by-product by weight is mixed with 103 pounds heptane condensate recycle to dissolve the heptane and the solution is fed to the top of the stripping zone of the column described in Example I. To the rectification zone of said column is fed 103 pounds of heptane condensate as reflux. The heptane condensate contains about 1.0 weight percent phenol and is at a temperature of 82° C. The partial reboiling zone of said column is operated at a temperature of 227° C. From the top of the column, there flows 224.8 pounds per hour of a mixture containing about 5% $BF_3$ gas, about 1.1% phenol vapor, about 1.2% red oil complex, and about 92.7% heptane by weight at a temperature of 101.5° C. The condensate therefrom, at a temperature of 82° C, is mixed with 1.66 pounds fresh heptane to provide the above heptane recycle and reflux containing 1.0 weight percent phenol. The red oil is withdrawn from the condensate receiver for discard and amounts to about 2.6 pounds per hour.

The gaseous mixture containing about 0.37% HF, about 68% $BF_3$, and about 31.6% heptane is contacted with soft glass beads to remove HF and then fed at 17.8 pounds per hour into liquid phenol with 1.72 pounds per hour of make-up fresh $BF_3$ gas to provide the phenol feed to the alkylation reaction.

The $BF_3$-free fluid in the partial-reboiling zone of the column is withdrawn at 1408.5 pounds per hour and at its temperature of 227° C (viscosity of 7.8 cps) is charged to distillation for removal of phenol and then for removal of the $C_6$ alkyl-substituted phenol by-product. The final solution (still bottoms), 1237.9 pounds per hours, contains 48.7 weight percent of 941 $\overline{M}_n$ p-alkyphenol product, alkyl-sutstituent of 848 $\overline{M}_n$.

EXAMPLE III

In this example, phenol is alkylated as described in Example I but on a smaller scale and by diluting the butene copolymer with 44 weight percent SAE-5W oil. The copolymer and phenol reactants are dried before use. The alkylation reaction mixture is divided into portions A, B and C. Portion A is treated with ammonia to convert $BF_3$-phenolate to $BF_3$-ammonia solid complex. The complex is removed by filtration. The filtrate is washed with water, dried and then subjected to distillation to remove unreacted phenol and the t.amyl- and t.butyl-phenol by-products. The distillation residue contains about 49 weight percent of the desired p-alkylphenol product.

Portions B and C of the alkylation reaction mixture are processed as described in Example I with the following exception. Portion B and 7.5 weight percent n-heptane are mixed to dissolve n-heptane at 55° C and the solution is fed to a five plate efficiency column as in Example I. The partial-reboiler for said column is operated at 250° C. No n-heptane is added as reflux to the column during the $BF_3$ removal from Portion B. Portion C cooled to 55° C but without n-heptane is fed to a five plate efficiency column whose partial-reboiler is operated at 250° C, but 7.5 weight percent n-heptane is added as reflux to the rectification zone of the column during $BF_3$ removal. Otherwise Portions B and C were processed as described in Example I through removal of unreacted phenol and t.amyl- and t.butyl-phenol by-products by distillation. The distillation bottom products of Portions B and C each contain 44 weight percent of the desired p-alkyphenol product.

EXAMPLE IV

Again the alkylation of dry phenol with dry butene copolymer is conducted as described in Example I but the oil dilution of copolymer is about 48 weight percent instead of 32 weight percent. The alkylation reaction mixture is divided into Portions A, B and C and processed as described in Example III but using n-octane with Portions B and C. The final products of Portions A, B and C after removal of unreacted phenol and t.amyl- and t.butyl-phenols respectively contained 44, 43.5 and 34.8 weight percent of the desired p-alkylphenol product.

The results of using n-heptane and n-octane either in the feed to $BF_3$ removal or as reflux during $BF_3$ removal according to the processing of Portions B and C of Examples III and IV show that such exclusive uses favor the use of the 80°–125° C boiling alkane as dissolved in the feed rather than as reflux to the $BF_3$ removal step. However, the use of n-heptane both dissolved in two-thirds of the alkylation reaction mixture as feed and as reflux during $BF_3$ removal from the alkylation reaction mixture (48 weight percent oil on the butene copolymer) produced as described in Example IV provides a final product (Portions B and C so processed as single feed) containing 44.6 weight percent of the desired p-alkylphenol product compared to 44 weight percent thereof in the final product of Portion A. Removal of n-octane during removal of unreacted phenol and t.amyl- and t.butyl-phenols also removes some of the alkanes in the mixture contributed by the diluent oil or butene polymer. Thus the desired product content of 44.6% is higher than the 44% in the final product from Portion A.

The use of the 80°–125° C boiling alkane for $BF_3$ removal of the present inventive process appears to be enhanced by such alkane dissolved in the alkylation reaction mixture beyond mere in situ vaporization of the alkane. To demonstrate this, nitrogen gas injection is substituted for such alkanes during $BF_3$ removal otherwise conducted as described in Example I. That is, nitrogen gas is injected into the partial-reboiler vapors and no 80°–125° C boiling alkane is used in the feed or added as reflux. The reflux condenser is operated to condense phenol vapors to provide phenol condensate as reflux liquid. Two such nitrogen injections for $BF_3$ removal are conducted. The first ($N^1$) is conducted with an alkylation reaction mixture whose Portion A provides a final product (Portion A processed as described in Example III) containing 43 weight percent of p-alkylphenol product of 1623 M.W. The second ($N^2$) is conducted with an alkylation reaction mixture whose Portion A (processed as described with respect to Portion A of Example III) provides a final product containing 46.2 weight percent of p-alkylphenol of 1876 M.W. $BF_3$ removal by such nitrogen injections were conducted with 600 cc nitrogen per minute (a gas volume equivalent to 25 weight percent n-octane in the alkylation reaction mixture) for $N_1$ and 5000 cc nitrogen per minute for $N^2$. The final products, after removal of unreacted phenol and low molecular weight alkylphenol by-products, have for $N^1$ injection operation 33.4 weight percent of 1359 M.W. p-alkylphenol product and for $N^2$ operation 33.3 weight percent of 1681 M.W. p-alkylphenol product. The substantial loss of desired (1623 and 1876 M.W.) p-alkylphenol products resulted from the molecular weight degradations from 1623 to 1359 and from 1876 to 1681. Thus mere inertness of the $BF_3$ stripping agent during $BF_3$ removal is not the technical effect of the present inventive process even though inert nitrogen did effect removal of $BF_3$.

EXAMPLE V

The $BF_3$ removal process of Example I is repeated using an alkylation reaction mixture containing 41.6 weight percent of number average 1644 M.W. p-alkylphenol product (alkyl-substituent of 1550 M.W. from butene polymer). There is dissolved 25 weight percent of n-octane in the alkylation reaction mixture at 51.5° C provide feed to a 10-plate, Oldershaw type column of 50 mm internal diameter whose partial-reboiler is operated at a temperature within the range of 255°–260° C with previously prepared 1644 M.W. p-alkylphenol (41.6%) product free of $BF_3$. The 51.5° C feed (n-octane dissolved in alkylation reaction mixture) is continuously pumped to the top (10th) plate. $BF_3$ bottom product is continuously withdrawn from the partial-reboiler. The octane-$BF_3$ vapor-gas mixture from the top of the column is taken through a condenser at a temperature of 100° C to condense n-octane. $BF_3$ gas is absorbed in phenol. No n-octane is returned as reflux.

The operating temperature of the partial-reboiler is varied within the range of 225°–260° C to maintain the top plate temperature at 126°–126.5° C, the temperature of the fifth plate between 158° and 165° C, and the bottom plate at temperature of 240° C at ambient pressure.

Upon completion of $BF_3$ removal from the feed, the withdrawn bottom product (partial-reboiler fluid) is distilled to remove unreacted phenol and by-product (t.amyl- and t.butyl-) alkylphenols as top fraction. The bottom fraction (distillation residue) is found to contain 41.2 weight percent of 1651 number average molecular weight p-alkylphenol product having a 1557 $\overline{M}_n$ alkyl-substituent.

Less n-octane, about 12–15 weight percent total (6–7.5% in feed and 6–7.5% as reflux), can be used effectively in the $BF_3$ removal step of Example I and obtain a product substantially the same as described above.

COMPARATIVE EXAMPLES

In the process for $BF_3$ removal, the viscous fluid alkylation reaction mixture contains p-alkylphenol product of 1650 $\overline{M}_n$ (alkyl-substituent of 1556 $\overline{M}_n$). Four aliquot portions of the viscous alkylation reaction mixture are taken. Each portion is separately charged to the second tray of a two tray column having a reboiler charged with $BF_3$-free portion ($BF_3$ removed from one portion by complexing with ammonia and filtration). The alkane stripping aid is n-octane used in an amount of 25 weight percent of each portion charged. Processing of Portions 1 and 2 is accomplished by adding n-octane to the surface of the heated reboiler liquid. The condensates of n-octane are not returned as reflux to the reboiler or to the top tray; i.e., tray above the feed tray. Portion 3 is processed by adding liquid n-octane and its condensate to the feed tray for a total of 25 weight percent of the viscous liquid alkylation reaction mixture fed. The temperatures of the reboiler, feed tray and top tray are shown in the table below together with the molecular weight of the $BF_3$-free portion of the feeds.

|  | Temperature, ° C | | | Product |
| --- | --- | --- | --- | --- |
|  | Reboiler | Feed Tray | Top Tray | $\overline{M}_n$ |
| Portion 1 | 165 | 125 | 124 | 1574 |
| Portion 2 | 238 | 151 | 139 | 1778 |
| Portion 3 | 240 | 191 249 | 125 | 1396 |

Processing of Portion 1 with reboiler temperature at 165° C and tray temperatures of 125° and 124° C resulted in a large proportion of n-octane remaining in the $BF_3$-free liquid in the reboiler and a loss of 4.7% of product molecular weight. Processing of Portion 2 with reboiler temperature at 238° C and feed tray temperature at 151° C did not retain n-octane in the reboiler but removed lower molecular weight portion of the desired product to give an alkylphenol product of 1778 $\overline{M}_n$, but at a reduced yield. This means that a portion of the desired product was lost by excessive stripping by the n-octane vapors. Processing of Portion 3 at reboiler temperature of 240° C and liquid n-octane added to the feed tray caused the feed tray temperature to increase from 191° to 249° C during operation and thus brought about substantial, 15.4%, molecular weight degradation of the desired p-alkylphenol product. Therefore, neither of the foregoing processing techniques are suitable for $BF_3$ removal.

However, use of the same two tray column can be successful provided the n-octane is dissolved in the viscous fluid alkylation reaction mixture in amounts of from 10–15 weight percent thereof and the reboiler operated at a temperature to provide a feed tray temperature between 125° and 130° C.

The present inventive process has been illustrated with respect to satisfactory $BF_3$ removal from alkylation reaction mixtures containing 2168 $\overline{M}_n$ p-alkylphenol (2075 $\overline{M}_n$ alkyl-substituent) to 941 $\overline{M}_n$ p-alkylphenol (848 $\overline{M}_n$ alkyl-substituent) products. The present inventive process is equally effective for processing alkylation reaction mixtures containing other of the 475–2800 $\overline{M}_n$ alkyl-substituted p-alkylphenol products.

The invention claimed is:

1. A process for continuous removal of $BF_3$ from the viscous fluid alkylation reacton mixture obtained by the reaction at a temperature in the range of 45°–60° C of phenol with a 500–3000 $\overline{M}_n$ viscous liquid polymer of propylene or butylene in the presence of $BF_3$-phenolate catalyst and mineral oil of the crankcase lubricating viscosities, wherein for each mole of said polymer there is used 1–6 moles of phenol and 0.05 to 0.5 mole of said catalyst and mineral oil in an amount of 30–70 weight percent of said polymer; which $BF_3$ removal process comprises continously dissolving 6 to 25 weight percent of 80°–125° C boiling alkane hydrocarbon in the viscous liquid alkylation reaction mixture and continuously heating incremental portions of the resulting composition to a temperature in the range of from 100° to 130° C for simultaneous catalyst dissociation and vaporization of the alkane to strip $BF_3$ gas from the heated fluid with vapors of the alkane.

2. The process of claim 1 wherein said continuous heating is conducted by film flow of the composition over a heated surface.

3. The process of claim 1 wherein said continuous heating is conducted by continuous heat exchange between an increment of the composition and vapors of $BF_3$-free portion of the fluid alkylation reaction mixture generated at a temperature in the range of 150°–250° C.

4. The process of claim 3 wherein said continuous heat exchange is conducted in a stripping zone fed with the composition at a temperature of 45°–60° and the $BF_3$-free portion of the fluid alkylation reaction mixture from the stripping zone flows to and is heated to the temperature in the range of 150°–250° C in a partial-reboiling zone to generate said vapors for indirect heat exchange.

5. The process of claim 3 wherein the $BF_3$ gas is recovered and recycled for production of said catalyst by cooling in a partial-condensing zone the mixture of $BF_3$ gas and vapors of the alkane issuing from the stripping zone to condense from 50 to 97 percent of the alkane vapors and absorbing the uncondensed gas-vapor mixtures in liquid phenol at a temperature of up to 100° C.

6. The process of Claim 1 wherein the phenol and polymeric reactants have, respectively, water contents of 0.05 and 0.01 weight percent which water results in the formation of a red oil complex in the stripping zone portion of the below defined system of a combination of zones; the continuous removal and reuse of $BF_3$ comprising dissolving 80°–125° C boiling alkane in the viscous fluid alkylation reaction mixture in an amount of 6 to 12.5 weight percent of said viscous fluid at a temperature of from 45° to 60° C, feeding the resulting composition to the stripping zone of a system consisting of a combination of a partial-reboiling zone, a stripping zone, a rectification zone, a partial-condensing zone, a condensate receiving zone, and a zone for absorbing HF; heating the $BF_3$-free portion of the fluid alkylation reaction mixture flowing from the stripping zone to the partial-reboiling zone to a temperature in the range of from 150°–250° C, contacting said feed composition in the stripping zone with vapors from the partial-reboiling zone to heat by direct heat exchange said composition to the temperature of 100° to 130° C, adding additional 80°–125° C boiling alkane in an amount of from 6 to 12.5 weight percent of the fluid alkylation reaction mixture as reflux liquid to the rectification zone for contact therein with the gas-vapor mixture from said heating in the stripping zone, condensing 50–97 percent of the 80°–125° C boiling alkane in the partial-condensing zone, collecting and settling said condensate in the condensate receiving zone, discarding the red oil lower layer and recycling to the rectification zone the alkane condensate reflux liquid, contacting the uncondensed gas-vapor mixture with an HF absorbent, and adsorbing the HF-free gas-vapor mixture in liquid phenol at a temperature of up to 100° C to reform said catalyst and condense the remaining alkane vapors.

7. The process of claim 6 wherein the 80°–125° C boiling alkane is n-heptane and the amount thereof dissolved in the viscous fluid alkylation reaction mixture provided as liquid reflux to the rectification zone are both seven weight percent of the fluid alkylation reaction mixture, the HF absorbent is soft glass, the partial-reboiling zone is heated to a temperature of 250° C, and 97% of n-heptane is condensed in the partial-condensation zone.

* * * * *

UNITED STATES PATENT OFFICE
CERTIFICATE OF CORRECTION

Patent No. 4,017,548　　　　　　　　　Dated April 12, 1977

Inventor(s) DENNIS G. PETRILLE

It is certified that error appears in the above-identified patent and that said Letters Patent are hereby corrected as shown below:

In the patent at:

Col. 1, line 33, "Sepcification" should read --Specification-- per application page 2, line 5.

Col. 2, line 20, "475-1800 M.W." should read --475-2800 M.W.-- per application page 3, line 16.

Col. 3, lines 60-61 "poymeric" should read --polymeric-- per application page 6, line 8.

Col. 5, line 7 "80° 125°C" should read --80°-125°C-- per application page 8, line 8.

Col. 6, line 9 "and be" should read --can be-- per application pg. 9, line 29

Col. 6, line 11 "viscuous" should read --viscous-- per application page 9, line 30.

Col. 6, line 55, "150-250°°C" should read --150-250°C-- per application page 11, line 2.

UNITED STATES PATENT OFFICE
CERTIFICATE OF CORRECTION

Patent No. 4,017,548          Dated April 12, 1977

Inventor(s) DENNIS G. PETRILLE

It is certified that error appears in the above-identified patent and that said Letters Patent are hereby corrected as shown below:
CONT'D.

Col. 6, line 56 "protion" should read --portion-- per application page 11, line 3.

Col. 7, line 19 "dissocaited" should read --dissociated-- per application page 11, line 25.

Col. 8, line 3, "137-138° liberate C" should read --137-138°C-- per application page 13, line 3.

Col. 8, line 4 "liberte" should read --liberate-- per appln. pg. 13, line 3.

Col. 8, line 51 "conensing" should read --condensing-- per appln. pg. 14, line 7.

Col. 9, line 56, "dissovled" should read --dissolved-- per appln. pg. 16, line 1.

Col. 10, line 28 "tetrafuoride" should read --tetrafluoride-- per appln. page 17, line 1.

UNITED STATES PATENT OFFICE
CERTIFICATE OF CORRECTION

Patent No. 4,017,548　　　　　　　　　Dated April 12, 1977

Inventor(s)　　DENNIS G. PETRILLE

It is certified that error appears in the above-identified patent and that said Letters Patent are hereby corrected as shown below:
CONT'D. page 3

Col. 10, line 38 "prcent" should read --percent-- per appln. page 17, line 9.

Col. 11, line 6 "an 87" should read --and 87-- as shown in application page 18, line 5.

Col. 11, line 40 "4.6% heptane" should read --44.6% heptane-- per appln. page 19, line 3.

Col. 12, line 52, "alkyl-sutstituent" should read --alkyl-substituent-- per appln. page 21, line 4.

Col. 14, line 4, "$BF_3$ removal" should begin new paragraph at this point as shown in appln. page 23, line 11.

Col. 14, line 28, "Cprovide" should read --C to provide-- per application page 23, line 29.

Signed and Sealed this

First Day of November 1977

[SEAL]

Attest:

RUTH C. MASON　　　　　　　　　LUTRELLE F. PARKER
Attesting Officer　　　　　Acting Commissioner of Patents and Trademarks